(12) United States Patent
Solar et al.

(10) Patent No.: US 8,170,645 B2
(45) Date of Patent: May 1, 2012

(54) FIDUCIAL MARKER AND PROTECTIVE CAP

(75) Inventors: Matthew S. Solar, Indialantic, FL (US); Mark Stephen Freas, Palm Bay, FL (US); Thomas L. Bridges, Melbourne Beach, FL (US); David M. Lee, Melbourne Beach, FL (US)

(73) Assignee: Medtronic, Inc., Minneapolis, MN (US)

( * ) Notice: Subject to any disclaimer, the term of this patent is extended or adjusted under 35 U.S.C. 154(b) by 1080 days.

(21) Appl. No.: 11/597,270

(22) PCT Filed: Jun. 7, 2005

(86) PCT No.: PCT/US2005/020009
§ 371 (c)(1), (2), (4) Date: Jul. 19, 2007

(87) PCT Pub. No.: WO2005/120380
PCT Pub. Date: Dec. 22, 2005

(65) Prior Publication Data
US 2007/0260140 A1 Nov. 8, 2007

Related U.S. Application Data

(60) Provisional application No. 60/577,548, filed on Jun. 7, 2004.

(51) Int. Cl.
*A61B 5/05* (2006.01)
(52) U.S. Cl. ......... 600/426; 606/302; 606/308; 606/309
(58) Field of Classification Search ................... 600/426; 606/916, 308, 309, 302
See application file for complete search history.

(56) References Cited

U.S. PATENT DOCUMENTS

| 5,480,410 | A | 1/1996 | Cuschieri et al. |
| 5,906,463 | A * | 5/1999 | Damm et al. ................. 411/369 |
| 5,913,847 | A | 6/1999 | Yoon |
| 6,551,270 | B1 | 4/2003 | Bimbo et al. |
| 6,730,081 | B1 * | 5/2004 | Desai ............................... 606/40 |
| 6,942,667 | B1 * | 9/2005 | Song ............................. 606/916 |
| 7,255,713 | B2 * | 8/2007 | Malek ......................... 623/17.12 |
| 2003/0120276 | A1 * | 6/2003 | Tallarida et al. ................ 606/61 |
| 2004/0019265 | A1 * | 1/2004 | Mazzocchi et al. ........... 600/407 |
| 2004/0030236 | A1 | 2/2004 | Mazzocchi et al. |
| 2004/0068260 | A1 | 4/2004 | Cossette et al. |
| 2006/0281991 | A1 * | 12/2006 | Fitzpatrick et al. ........... 600/426 |

FOREIGN PATENT DOCUMENTS
WO WO-2005120380 A1 12/2005

* cited by examiner

*Primary Examiner* — Brian Casler
*Assistant Examiner* — Daniel Huntley
(74) *Attorney, Agent, or Firm* — Harness, Dickey & Pierce, PLC

(57) ABSTRACT

This document discusses, among other things, a fiducial marker kit. In one example, the kit includes a fiducial marker assembly that includes a bone screw base for receiving an imageable marker or locatable divot. A valved protective sleeve prevents debris from accumulating in a receptacle portion of the base, which may otherwise degrade the accuracy of patient registration in an image-guided surgical procedure. In one example, the valve automatically opens or closes upon insertion or removal of a screwdriver or other tool, or a shaft portion of the imageable marker or locatable divot. Various bone screw base and receptacle combinations are also discussed.

18 Claims, 11 Drawing Sheets

FIDUCIAL MARKER AND PROTECTIVE CAP

RELATED APPLICATIONS

This application is a nationalization under 35 U.S.C. 371 of PCT/US2005/020009, filed Jun. 7, 2005 and published as WO 2005/120380 A1, on Dec. 22, 2005, which claimed priority under U.S.C. 119(e) to U.S. Provisional Patent Application No. 60/577,548, filed Jun. 7, 2004, which applications and publication are incorporated herein by reference and made a part hereof.

TECHNICAL FIELD

This document relates generally to imaging and/or locating a subject, such as for performing surgical intervention, and more specifically, but not by way of limitation, to fiducial marker devices and associated devices, tools, and methods.

BACKGROUND

Fiducial markers that can be located and recognized by an imaging system or other system are useful in neurosurgery and other applications. Examples of imaging system modalities include, among other things, magnetic resonance imaging (MRI), computed tomography (CT), positron emission tomography (PET), and single photon emission computed tomography (SPECT).

For example, in one technique, multiple fiducial markers are screwed into the patient's skull to define landmarks recognizable by an imaging system. The imaging system is used to obtain one or more preoperative images of the patient's brain. Recognizable images of the fiducial markers appear on such preoperative images. Such a bone-anchored fiducial marker typically includes an externally threaded bone-screw portion, which is driven into the skull. A threaded shaft rises up and out of the skull from the bone-screw. The threaded shaft typically receives a screwed-on imagable sphere that is visible on an MRI or CT image. The multiple fiducial markers on the patient's skull define landmarks on preoperative images that are useful to the physician for planning entry coordinates on the patient's skull and for planning a trajectory to a target location in the brain. An image-guided surgical workstation uses these preoperative images and the planning data to guide the neurosurgeon while actually performing the subsequent surgical procedure.

After the preoperative planning phase, the patient is brought into the operating room so that the planned surgical procedure can be performed. On the operating table, the patient's skull is clamped in a head-frame or otherwise immobilized. In order to use the preoperative images provided by the image-guided workstation to guide the surgeon during the surgical procedure, the patient's skull must first be "registered" to the preoperative images. The registration creates an association between (1) the actual physical location of the fiducial markers on the patient's skull in the operating room and (2) the locations of the images of the fiducial markers visible on the preoperatively-obtained images. This allows mapping between the actual space in which the patient is located to the space defined by the preoperative images.

According to one registration technique, a "wand" is used to perform this patient registration. The wand typically includes multiple light-emitting diode (LED) locators or reflective locators, which are visible to an infrared camera or other detector of an optical positioning system in the operating room. The camera and optical positioning system are operatively connected to the image-guided workstation. The locators define the position of the wand in the operating room, including the position of a sharp tip portion of the wand, which is in a known physical relationship to the locators. To register the patient, the imagable spheres are unscrewed from the fiducial marker shafts, and replaced by respective "divots" that are sized and shaped to receive the wand tip in a recess that is shaped to mate with the wand tip. These divots are screwed or otherwise engaged onto the respective fiducial marker shafts, such that when the wand tip is received into the maximum depression point of the divot, the wand tip then corresponds to the same location as the center of the imagable sphere when the imagable sphere was screwed onto the fiducial marker shaft. A reference divot is typically also present in the operating room at a known location, such as attached to the operating table or the patient's skull-immobilizing headframe. During the patient registration process, the surgeon touches the wand tip to the reference divot (to provide an absolute positional reference to the image-guided workstation), and then to each fiducial marker divot. This permits the image-guided workstation to correlate the actual physical location of the patient's skull to the preoperative images. The physician can then use the wand, in conjunction with the preoperative images provided by the image-guided workstation, to locate an appropriate entry point and trajectory to the target in the brain.

The present inventors have recognized an unmet need for improved fiducial marker devices, tools, and methods.

SUMMARY

In one example, this document describes, among other things, a fiducial marker assembly for an image-guided surgical procedure. The fiducial marker assembly comprises a bone screw base. The base includes a distal threaded bone screw shaft and a proximal head. The fiducial marker assembly also comprises a protective sleeve, sized and shaped to fit securely directly or indirectly about the head of the bone screw base. The protective sleeve includes a proximal valve and an internal passage between the valve and the proximal head of the bone screw base.

This document also describes variations on this or other examples. In one variation, the fiducial marker assembly comprises a tubular cylindrical spacer secured to the proximal head of the bone screw base. The spacer is located between the proximal head of the bone screw base and the protective sleeve. In another variation, the valve includes a compliant material that automatically opens upon insertion of an object therein and automatically closes upon removal of the object therefrom. In another variation, the valve includes a cap that is sized and shaped to be manually pressed onto a proximal end of the protective sleeve to prevent debris from entering the passage of the protective sleeve. In another variation, the fiducial marker assembly includes an imageable marker that is sized and shaped to be secured to the proximal head of the bone screw base. In another variation, the fiducial marker assembly comprises a locatable divot that is sized and shaped to be secured to the proximal head of the bone screw base.

In another example, this document describes a protective sleeve that is sized and shaped to fit about a portion of a fiducial marker base. The protective sleeve includes a compliant valve that automatically opens upon insertion of an object into the valve and that automatically closes upon removal of the object from within the valve.

This document also describes variations on this or other examples. In one variation, the sleeve includes a distal flange that is sized and shaped to be disposed under a scalp to retain the sleeve in place with respect to the fiducial marker base. In another variation, the sleeve includes a lip that is sized and shaped to engage a portion of the fiducial marker head. In another variation, the sleeve includes an external coating, such as an aseptic or hydrophilic coating.

In another example, this document describes a kit. The kit comprises a bone screw base. The base includes a distal threaded bone screw shaft and a proximal head. The base also includes a protective sleeve. The protective sleeve is sized and shaped to fit securely directly or indirectly about the head of the bone screw base. The protective sleeve includes a proximal valve and an internal passage between the valve and the proximal head of the bone screw base.

This document also describes variations on this or other examples. In one variation, the kit comprises an imageable marker that is sized and shaped to be secured to the proximal head of the bone screw base. In another variation, the kit comprises a locatable divot that is sized and shaped to be secured to the proximal head of the bone screw base.

In one example, this document also describes a method. The method includes affixing a bone screw base to a skull. The base includes a valved sleeve located in association therewith. The method also includes attaching an imageable marker to the bone screw base, including inserting a portion of the imageable marker through a valve in the sleeve. The method also includes replacing the imageable marker with a locatable divot. The replacing includes removing the imageable marker and inserting the locatable divot through the valve.

This document also describes variations on this or other examples. In one variation, the method includes inserting the portion of the imageable marker through the valve such that this automatically opens the valve by compliant expansion of the valve, and such that removing the imageable marker includes automatically closing the valve by compliant relaxation of the valve.

This summary is not intended to be an exhaustive description of the described subject matter or claims, the details of which are included below.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
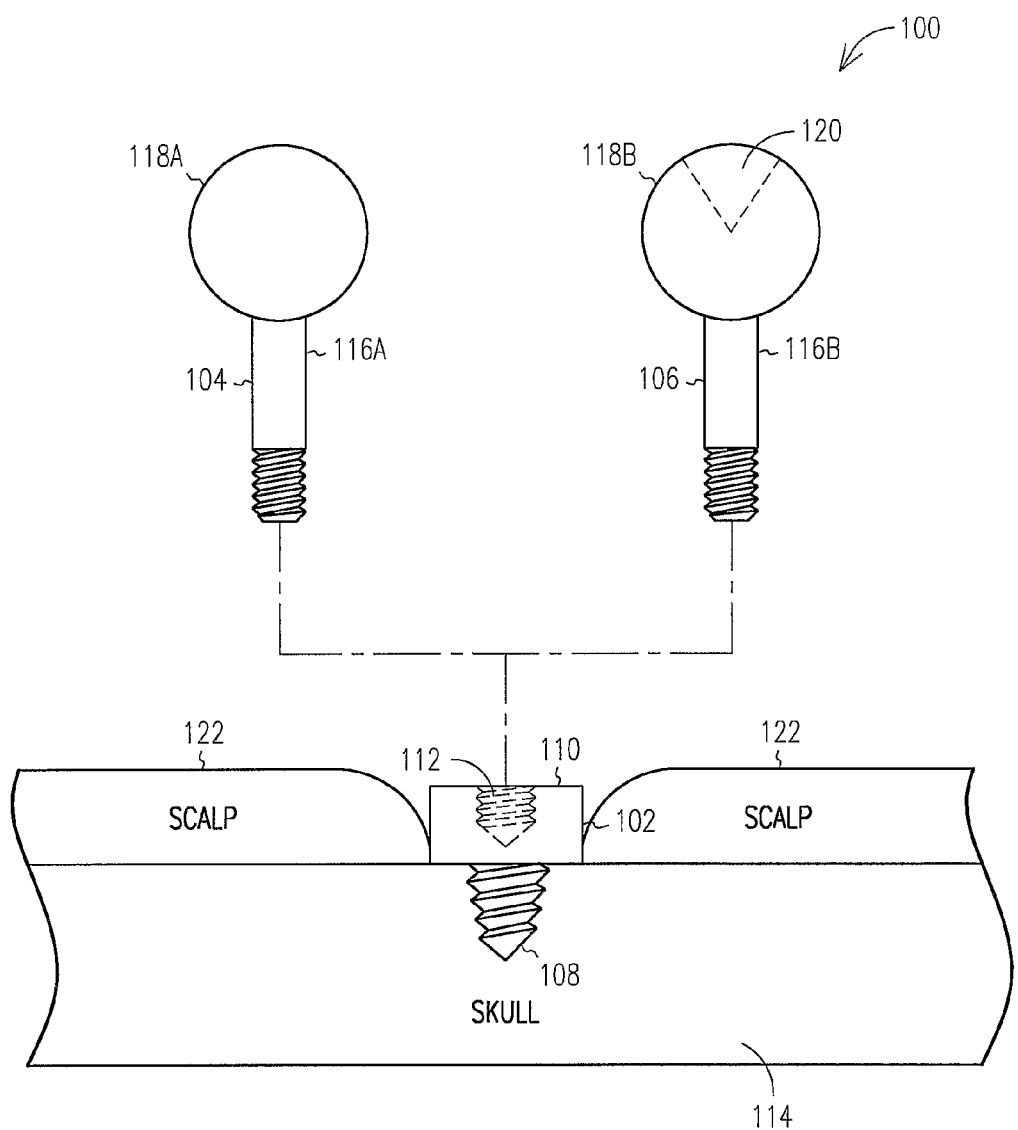
FIG. 1 is a schematic diagram illustrating generally one example of a fiducial marker assembly.

FIG. 1 is a schematic diagram illustrating generally one example of a fiducial marker assembly 100. In this example, the fiducial marker assembly 100 includes a bone screw base 102. The bone screw base 102 interchangeably receives one of an imagable marker 104 or a locating divot 106. In this example, the base 102 includes a distal self-tapping or other threaded bone screw shaft 108 and a proximal head 110. The head 110 includes a male or female receptacle 112 for receiving a corresponding portion of the imageable marker 104 or the divot 106. For example, FIG. 1 shows a internally threaded receptacle 112. The base 102 is driven into the skull 114, such as by using a threaded driver that fits into the threaded receptacle 112, or by using another driver that engages one or more other features of the head 110, such as screwdriver slots, hex heads, or the like.

In the example of FIG. 1, the imageable marker 104 and the divot 106 each have a shaft 116 and a head 118. The head 118A of the imageable marker 104 is imageable using the desired imaging modality. The head 118B of the divot 106 includes a receptacle 120 for receiving a locatable wand tip of a remote optical or other positioning system. When the imageable marker 104 is removed from the receptacle 112 of the base 102 and replaced by the divot 106, the point of maximum depression of the receptacle 120 of the divot 106 is located at the point that was previously occupied by the center of the imageable head 118A. Although the heads 118A-B are illustrated as generally spherical (with or without a conical recess), they could alternatively be cylindrical or various other desired shapes.

The imaging portion of an image-guided surgical procedure (e.g., using the imageable marker 104) may be performed at a different time than the registration portion of the procedure (e.g., using the imageable marker 106). During the intervening time, the scalp 122 may grow over or otherwise obscure the head 110 portion of the bone screw base 108. Moreover, blood or other debris may accumulate in the receptacle 112 during such intervening time. Such accumulation typically degrades the accuracy of the registration by blocking how far the shaft 116B of the divot 106 may be inserted into the receptacle 112. If the shaft 116B of the divot 106 is not inserted into the receptacle 112 as far as the shaft 116A of the imageable marker 104, then the point of maximum depression of the receptacle 120 will not be located at the point previously occupied by the center of the imageable head 118A.

Figure 2:
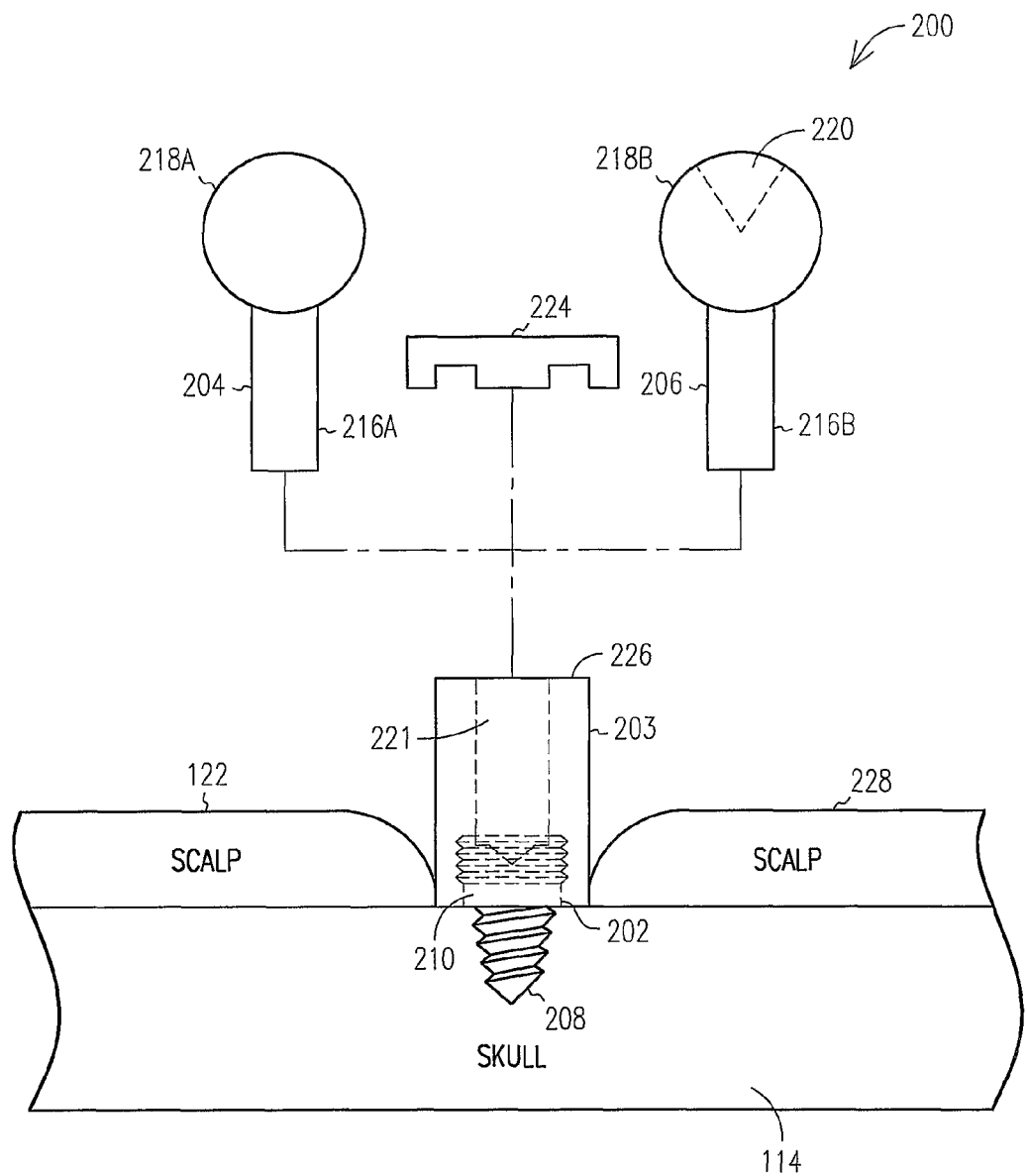
FIG. 2 is a schematic diagram illustrating generally an example of a similar fiducial marker assembly.

FIG. 2 is a schematic diagram illustrating generally an example of a similar fiducial marker assembly 200. In this example, the fiducial marker assembly 200 includes a bone screw base 202 having an attachable, detachable, or integral tubular cylindrical spacer 203. The spacer 203 interchangeably receives one of an imagable marker 204 or a divot 206. The base 202 includes a self-tapping or other threaded distal bone screw shaft 208 and a proximal head 210. In this example, the head 210 includes a slotted or Phillips receptacle 112 or the like. This permits a screwdriver or the like to drive the shaft 208 into the skull 114. In this example, the cylindrical spacer 203 includes an orifice 221 sized and shaped for snugly receiving a corresponding shaft portion of the imageable marker 204 or the divot 206. In the example of FIG. 2, the imageable marker 204 and the divot 206 each have a shaft 216 and a head 218. The head 218A of the imageable marker 204 is imageable using the desired imaging modality. The head 218B of the divot 206 includes a receptacle 220 for receiving a locatable wand tip of a remote optical or other positioning system. When the imageable marker 204 is removed from the receiving cylindrical orifice 221 of the spacer 203 and replaced by the divot 206, the point of maximum depression of the divot 206 is then located at the point previously occupied by the center of the imageable head 218A.

In this example, the cylindrical spacer 203 is tall enough to rise above the upper surface of the scalp 102. This makes it easier to find the fiducial marker assembly 200, such as when the imageable marker 204 has been removed during an intervening time between imaging and a later patient registration using the divot 206. However, the spacer 203 can still accumulate blood or other debris within the cylindrical orifice 221. This may degrade accuracy of the subsequent patient registration, as explained above. In one example, the fiducial marker assembly 200 is included in a kit that also provides a silicone or other at least somewhat compliant cap 224 as part of the fiducial marker assembly 200. The cap 224 is sized and shaped to be press fitted into or about the proximal end of the cylindrical spacer 203. The cap 224 prevents debris from accumulating within the cylindrical orifice 221. The cap 224 can be used whenever the cylindrical orifice 221 is not occupied by one of the imageable marker 204 or the divot 206, such as during the intervening time between imaging and patient registration, for example. In an alternative example, the cap 224 is instead configured as a cork-shaped stopper having a distal end that fits within the cylindrical orifice 221. In yet another alternative example, the spacer 208 is of a height that makes its proximal surface 226 flush with, or even recessed from, the outer surface 228 of the scalp 122.

Figure 4:
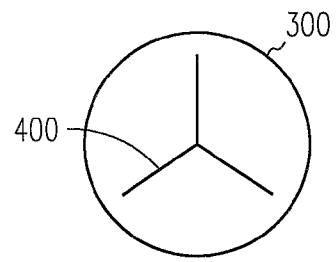
FIG. 4 is a schematic diagram illustrating a top view of a sleeve, including a valve.
Figure 3:
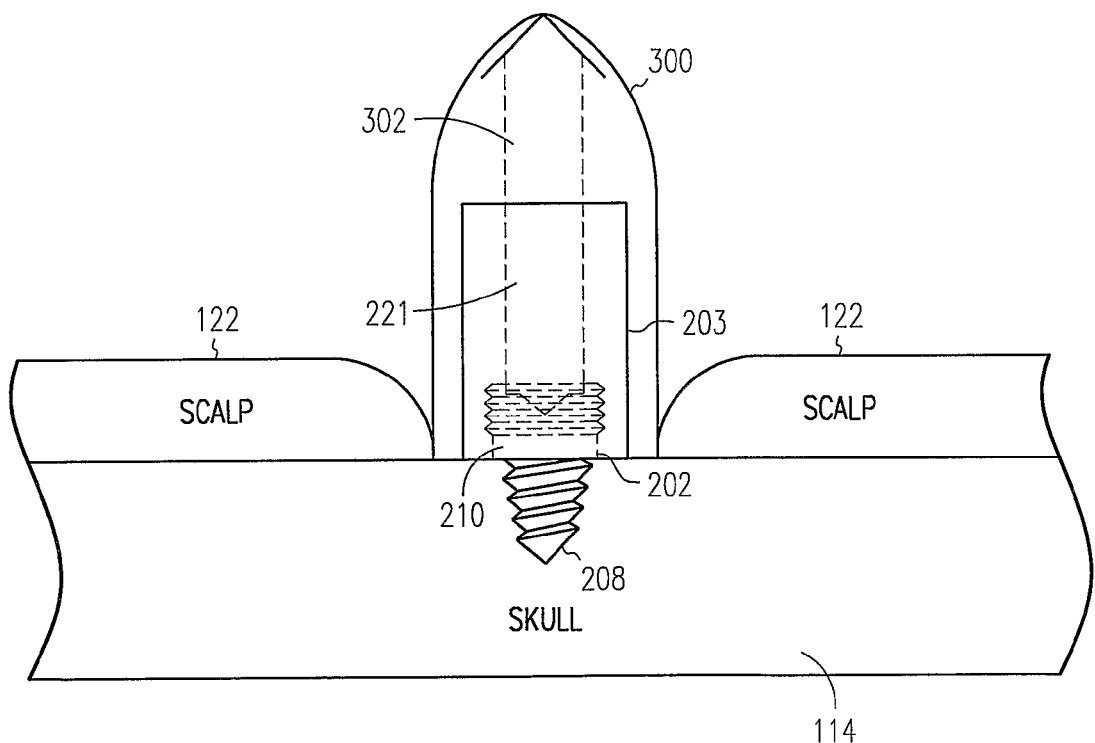
FIG. 3 is a schematic diagram illustrating generally one example of a silicone or other at least somewhat compliant protective sleeve placed about a base or a spacer.

FIG. 3 is a schematic diagram illustrating generally one example of a silicone or other at least somewhat compliant protective sleeve 300 placed about the base 202 or the spacer 203. FIG. 4 is a schematic diagram illustrating a top view of the sleeve 300, including at least one slit or other valve 400, such as the tricuspid valve illustrated in FIG. 4. In this example, the compliant sleeve 300 fits snugly and securely about the spacer 203. In this example, the compliant valve 400 automatically opens when a screwdriver or other tool, or when a shaft of an imageable marker or locatable divot is inserted therein. The valve 400 automatically closes when the tool is withdrawn. In this way, the valved sleeve 300 prevents debris from accumulating within the orifice 221 of the spacer 203 or within the receptacle of the base 202. The valve 400 includes a lumen or other passage 302 through which such tool is inserted to drive the base 202 into the skull 114, and through which a shaft of an imageable marker or locatable divot can be inserted. The compliant sleeve 300 fits snugly enough around the spacer 203 (or alternatively, directly around the base 202) such that it does not pull free when the driver or other tool is withdrawn from the valve 400, thereby automatically closing the valve 400. However, in one example, the sleeve 300 is compliant enough such that it can be removed after the base 202 is secured into the skull 114.

In one example, the sleeve 300 is first fitted about the spacer 203 or base 202 even before the base 202 is driven into the skull 114, and the driver is inserted into the sleeve 300. This advantageously holds the base 202 or spacer 203 to the tip of the driver. This makes it easier to insert the base 202 into the skull 114. For example, there is no need to separately hold the base 202 in place against the skull 114 until the driver can be inserted into the base 202 and the base 202 begins to bite into the skull 114.

In various examples, the sleeve 300 is made from polyurethane, polyethylene, polypropylene, biomedical grade silicone rubber, Santoprene®, or any other suitable material. In various examples, the sleeve 300 is made using injection molding, extrusion, or any other suitable process. In one example, the valve 400 is then cut into the sleeve 300 after it is formed.

Figure 6:
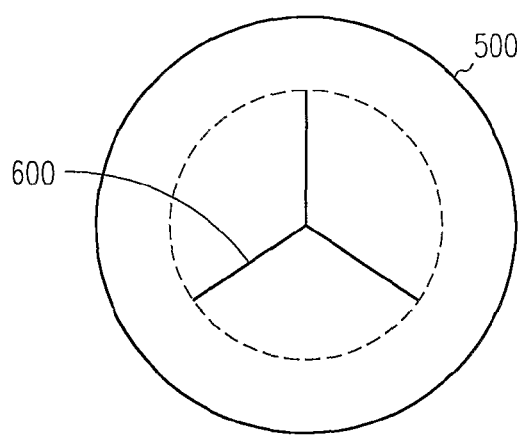
FIG. 6 is a top view of the sleeve of FIG. 5, including a valve.
Figure 5:
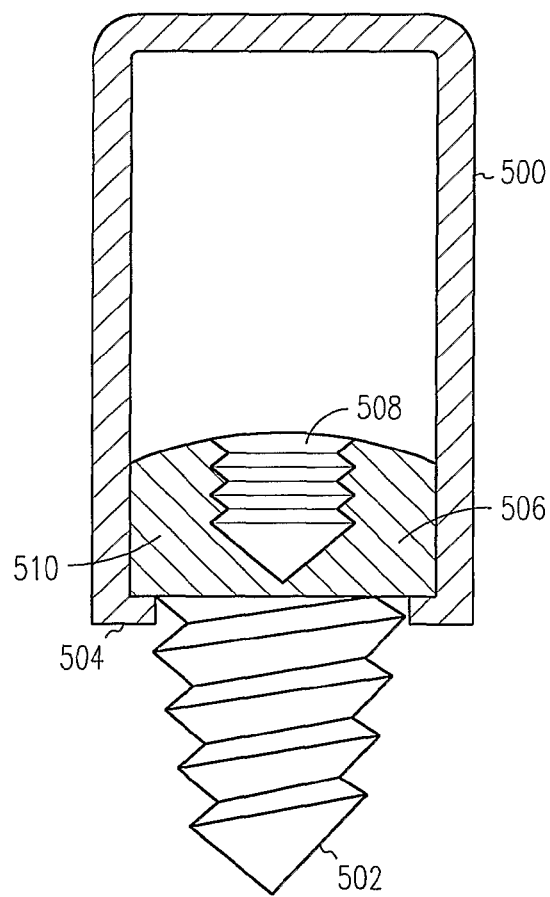
FIG. 5 is a schematic diagram illustrating generally an example of a similar valved compliant protective sleeve that is coupled directly to a bone screw base, such as by a lip that extends at least partially under a head portion of the base.

FIG. 5 is a schematic diagram illustrating generally an example of a similar valved compliant protective sleeve 500 that is coupled directly to a bone screw base 502, such as by a lip 504 that extends at least partially under a head 506 portion of the base 502. In this example, an imageable marker or locatable divot is threaded, snap-fitted, or otherwise inserted into a receptacle 508 in a head 510 portion of the base 502, similar to the example shown in FIG. 1. FIG. 6 is a top view of the sleeve 500, including a tricuspid or other compliant valve 600.

Figure 8:
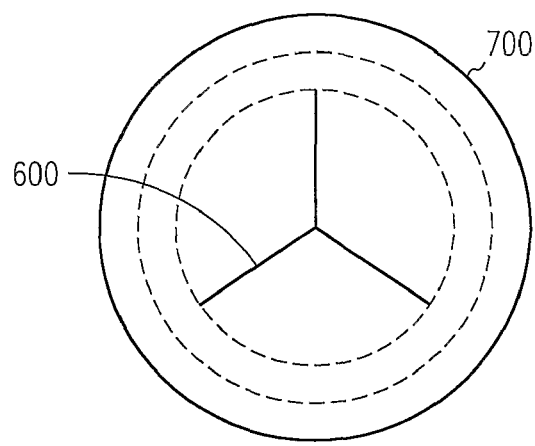
FIG. 8 is a top view of the sleeve of FIG. 7, including a valve.
Figure 7:
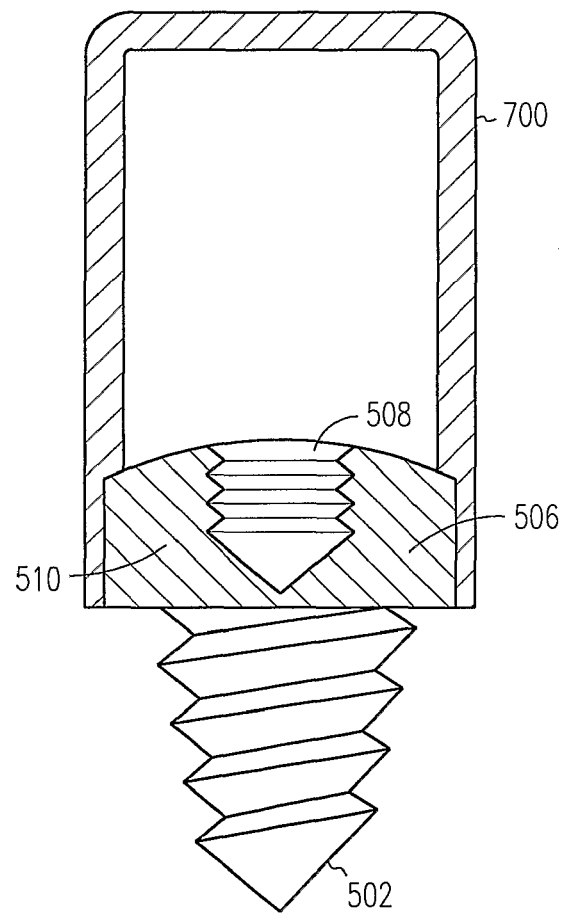
FIG. 7 is a schematic diagram illustrating generally an example of a similar valved compliant protective sleeve that is snugly coupled directly about a bone screw base without using a lip.

FIG. 7 is a schematic diagram illustrating generally an example of a similar valved compliant protective sleeve 700 that is snugly coupled directly about a bone screw base 502 without using the lip 504 of FIG. 5. In this example, an imageable marker or locatable divot is threaded, snap-fitted, or otherwise inserted into a receptacle 508 in a head 510 portion of the base 502, similar to the example shown in FIG. 1. FIG. 8 is a top view of the sleeve 700, including a tricuspid or other compliant valve 600.

Figure 10:
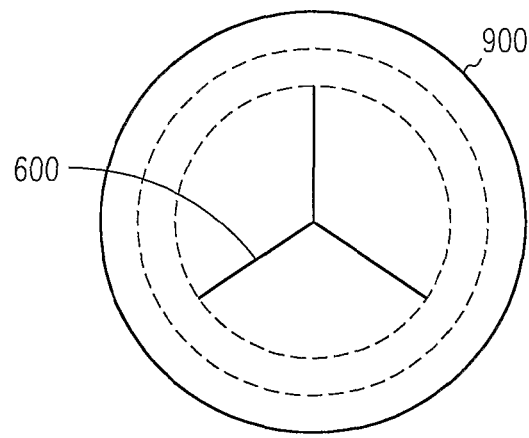
FIG. 10 is a top view of the sleeve of FIG. 9, including a valve.
Figure 9:
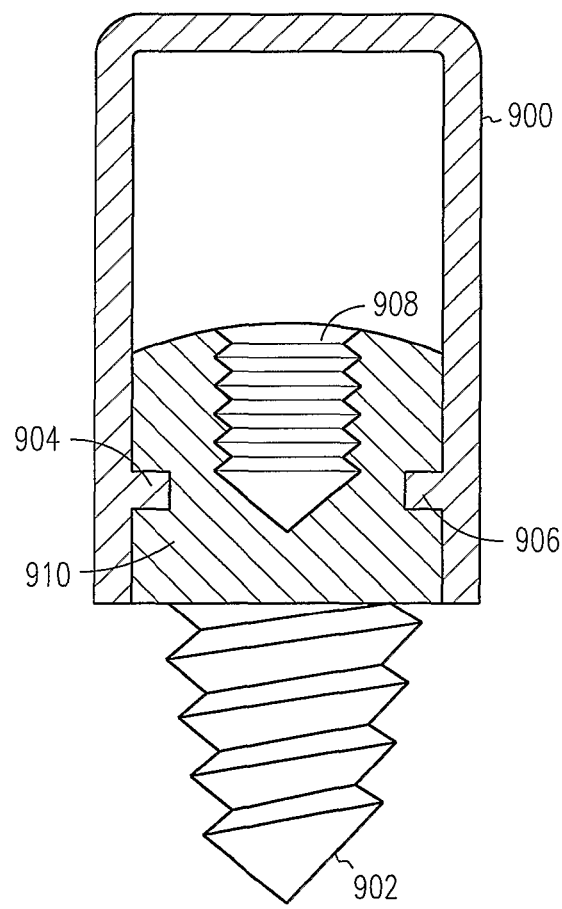
FIG. 9 is a schematic diagram illustrating generally an example of a similar valved compliant protective sleeve that is snugly coupled directly about a bone screw base using an inner circumferential lip.

FIG. 9 is a schematic diagram illustrating generally an example of a similar valved compliant protective sleeve 900 that is snugly coupled directly about a bone screw base 902 using an inner circumferential lip 904 that engages a corresponding outer circumferential groove 906 in a head 910 portion of the base 902. Alternatively, the lip 904 and groove 906 can be exchanged such that the lip is part of the head 910 portion of the base 902 and the groove is part of the sleeve 900. In the example of FIG. 9, an imageable marker or locatable divot is threaded, snap-fitted, or otherwise inserted into a receptacle 908 in a head 910 portion of the base 902, similar to the example shown in FIG. 1. FIG. 10 is a top view of the sleeve 900, including a tricuspid or other compliant valve 600.

Figure 11:
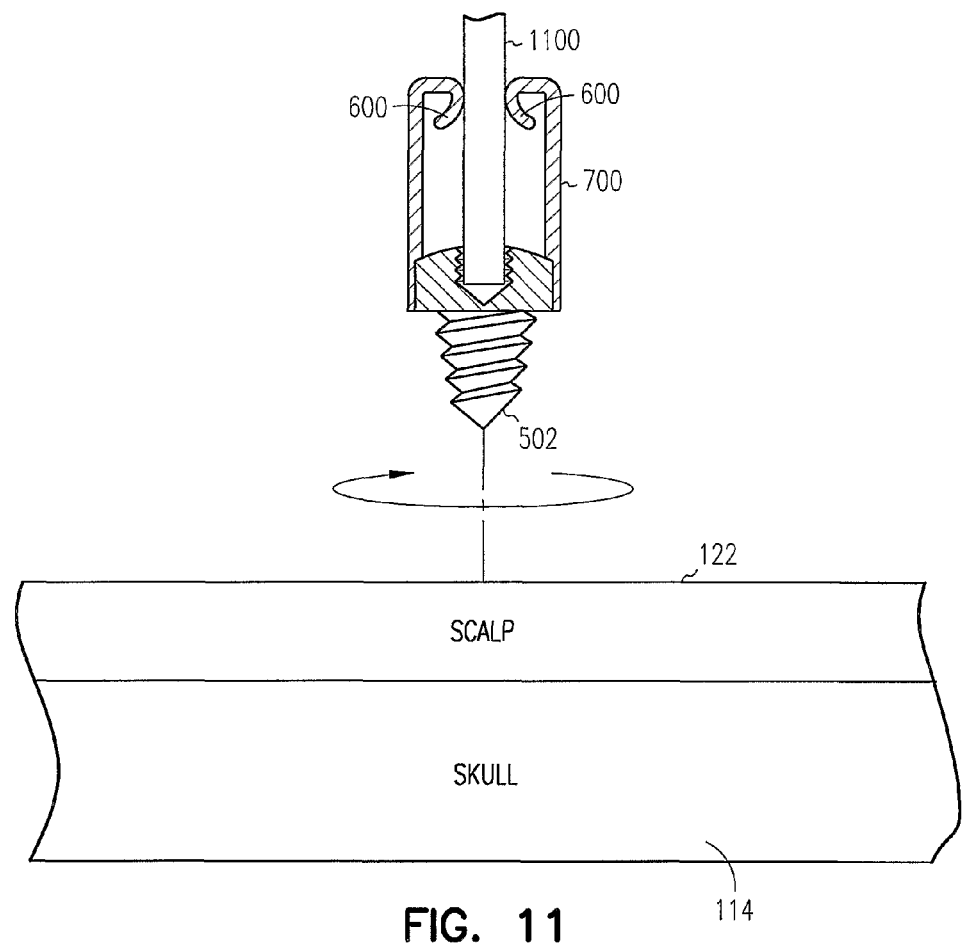
FIG. 11 is a cross-sectional schematic diagram illustrating one example of using a valved compliant protective sleeve with an object inserted through the valve to automatically open it.

FIG. 11 is a cross-sectional schematic diagram illustrating one example of using the valved compliant protective sleeve 700, with a screw driver tip 1100 having been inserted through the valve 600 to automatically open the valve 600. The compliance of the valve 600 advantageously holds the sleeve 700 and base 502 onto the screw driver tip 1100, making it easier to drive the base 502 into the skull 114.

Figure 12:
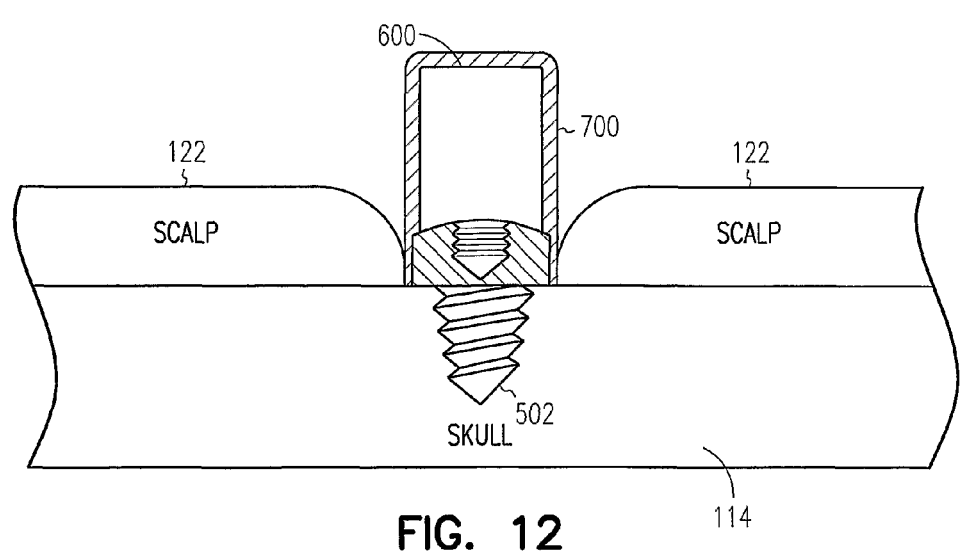
FIG. 12 is a cross-sectional schematic diagram illustrating the same example of using the valved compliant protective sleeve, in which the object has been withdrawn to automatically close the valve.

FIG. 12 is a cross-sectional schematic diagram illustrating the same example of using the valved compliant protective sleeve 700, in which the base 502 has been driven into the skull 114 and the driver tip 1100 has been withdrawn to automatically close the valve 600. In one example, one or more of the various valved compliant protective sleeves discussed in this document optionally incorporate a coating. One example includes an antiseptic or antibiotic coating to reduce infection or promote healing. Another example includes a hydrophilic coating or other lubricant for ease of insertion or to reduce or prevent adhesion of clotting blood or other substances to the sleeve 700. Examples include, among other things, polydimethylsiloxane (PDMS), such as Dow Corning 360 Medical Fluid, silicone oil, polyacrylomide or like hydrogels, or polyvinylpyrollidone. Other examples of lubricating coatings include, among other things, polyethylene oxide (PEO), polyhydroxyethyl methacrylate (PHEMA), or polyvinyl alcohol (PVA).

Figure 14:
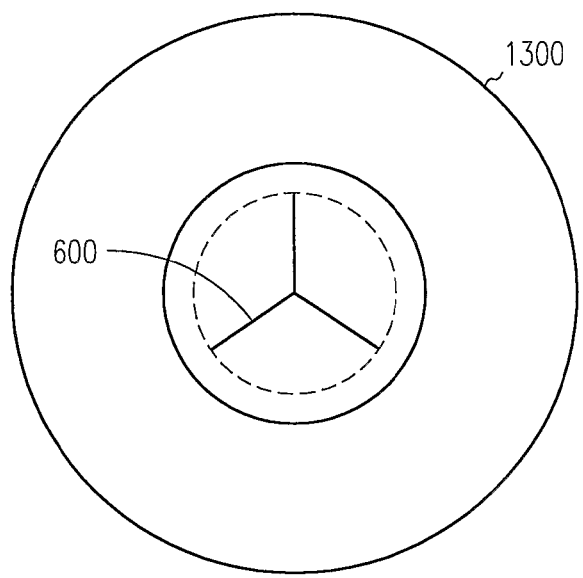
FIG. 14 is a top view of the sleeve of FIG. 13, including a valve.
Figure 13:
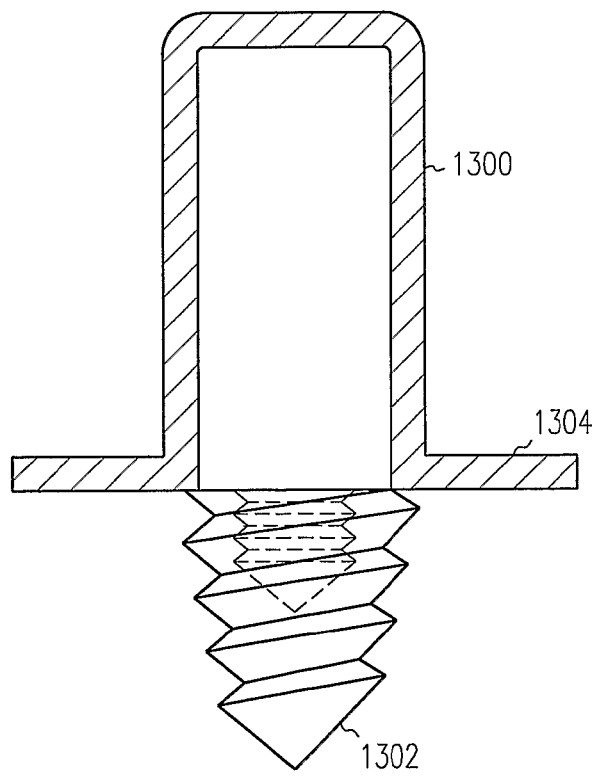
FIG. 13 is a cross-sectional schematic diagram illustrating one example of a flush-mounted base and a valved compliant protective sleeve with a flange that is placed beneath the scalp to hold the sleeve in place.
Figure 15:
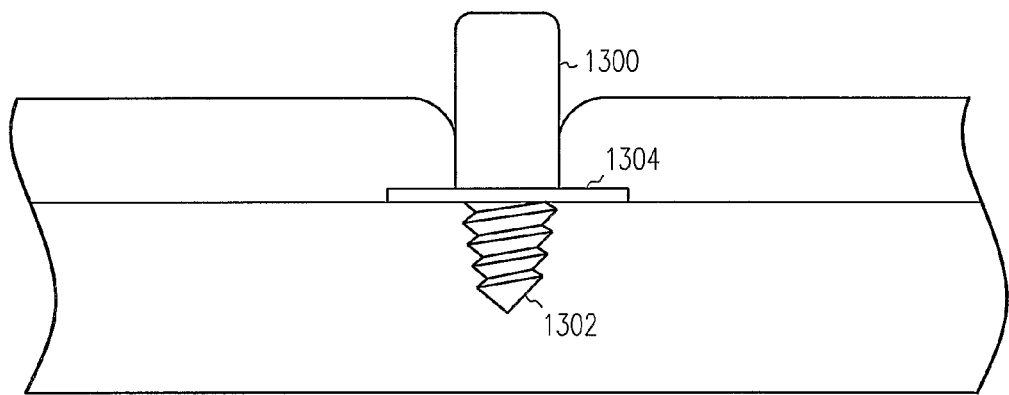
FIG. 15 is a cross-sectional schematic diagram illustrating the implanted base of FIG. 13, including the valved compliant protective sleeve with the flange in place under the scalp.

FIG. 13 is a cross-sectional schematic diagram illustrating one example of a flush-mounted base 1300 that does not have a head or other flanged portion to overlay a portion of the skull about which the screw shaft of the base 1300 is driven. Examples of flush-mounted fiducial marker bases are described in Matthew S. Solar U.S. patent application Ser. No. 10/206,884 entitled FIDUCIAL MARKER DEVICES, TOOLS, AND METHODS, which was filed on Jul. 29, 2002, and which is incorporated herein by reference in its entirety, including its discussion of flush-mounted fiducial marker bases. The example of FIG. 13 includes a valved compliant protective sleeve 1302 with a distal base flange 1304 that is inserted beneath the scalp 122 to hold the sleeve 1302 in place. FIG. 14 is a top view of the sleeve 1302 including a tricuspid or other valve 600. FIG. 15 is a cross-sectional schematic diagram illustrating the implanted base 1300 including the valved compliant protective sleeve 1302 with the flange 1304 in place under the scalp 122.

Figure 16:
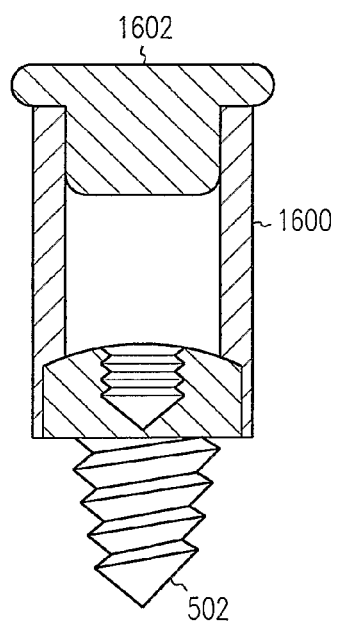
FIG. 16 illustrates an example of a valved tubular protective sleeve that includes a manually operated valve, such as a cap.
Figure 17:
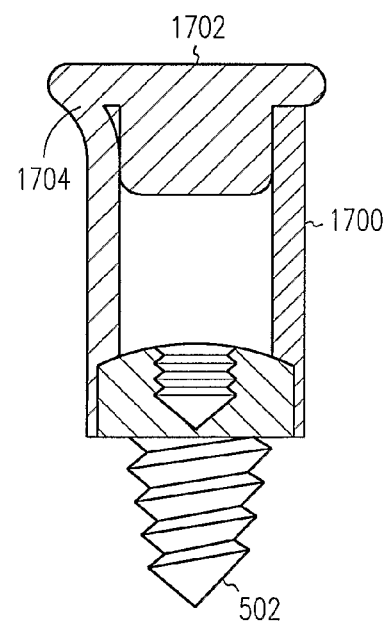
FIG. 17 illustrates an alternative example in which a manually attachable and detachable cap is integrally attached to a sleeve.

FIG. 16 illustrates an example of a valved tubular protective sleeve 1600 that includes a valve that does not automatically open and close upon insertion of a screwdriver tip or other tool through the valve. Instead, in this example, the valve takes the form of a cap 1602 that fits into or about a proximal end of the sleeve 1600. Because the cap is manually attached to or detached from the sleeve 1600, it typically does not require as much elasticity as the automatic valves described above. FIG. 17 illustrates an alternative example in which a manually attachable and detachable cap 1702 is integrally attached to a sleeve 1700, such as by a compliant tie 1704.

Figure 19:
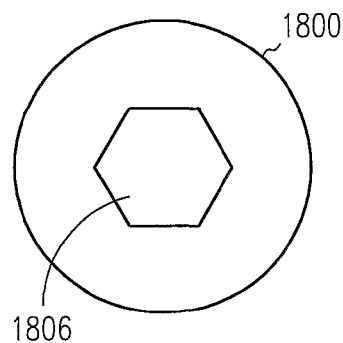
FIG. 19 illustrates a top view of the fiducial marker base of FIG. 18.
Figure 18:
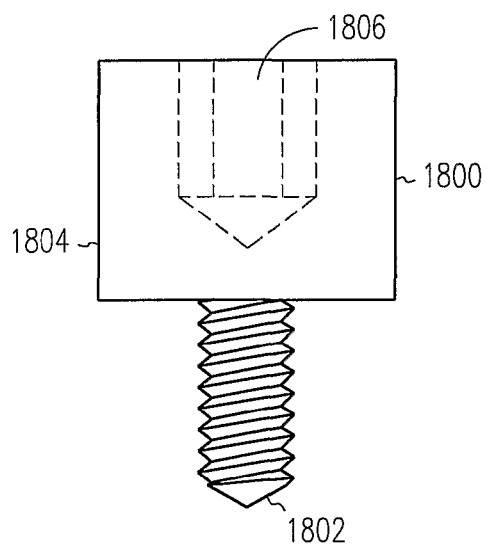
FIG. 18 is a cross-sectional schematic diagram illustrating generally one example of a fiducial marker base that includes an internal hexagonal or similar faceted orifice for being engaged by a corresponding driver or for a shaft portion of an imageable marker or locatable divot.

FIG. 18 is a cross-sectional schematic diagram illustrating generally one example of a fiducial marker base 1800 including an externally threaded distal shaft 1802 and a proximal head 1804 that includes an internal hexagonal or similar faceted orifice 1806 for being engaged by a corresponding driver to drive the base 1800 into the skull. In one example, a shaft portion of an imageable marker or locatable divot is correspondingly shaped so that it can be press or snap fitted into the same orifice 1806, which is also illustrated in the top view of FIG. 19.

Figure 21:
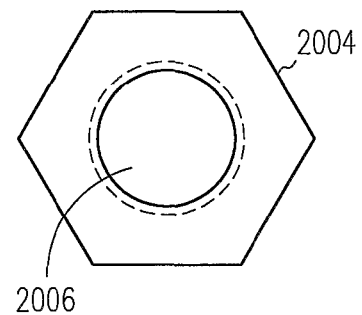
FIG. 21 illustrates a top view of the fiducial marker base of FIG. 20.
Figure 20:
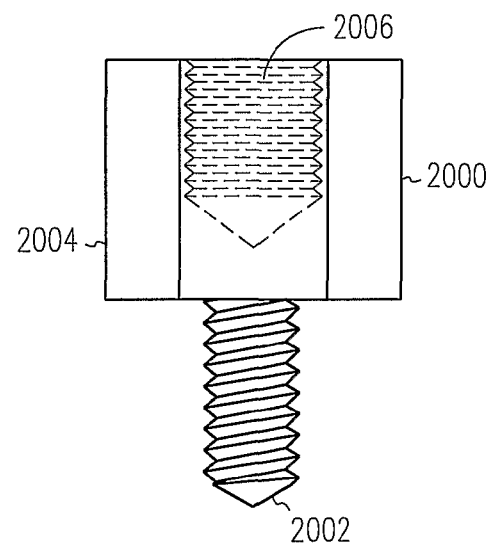
FIG. 20 is a cross-sectional schematic diagram illustrating generally one example of a fiducial marker base including a head that includes an external hexagonal or similar faceted surface for being engaged by a corresponding driver, and an internal orifice for receiving a shaft portion of an imageable marker or locatable divot.

FIG. 20 is a cross-sectional schematic diagram illustrating generally one example of a fiducial marker base 2000 including an externally threaded distal shaft 2002 and a proximal head 2004. In this example the proximal head 2004 includes an external hexagonal or similar faceted surface for being engaged by a corresponding driver to a drive the base 2000 into the skull. In one example, a shaft portion of an imageable marker or locatable divot is threaded into an internally threaded orifice 2006 in the head 2004, which orifice 2006 is also illustrated in the top view of FIG. 21.

Figure 23:
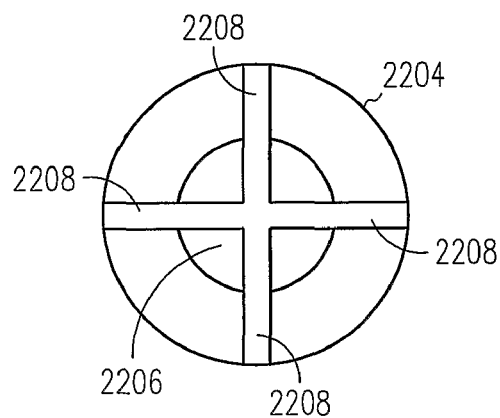
FIG. 23 illustrates a top view of the fiducial marker base of FIG. 22.
Figure 22:
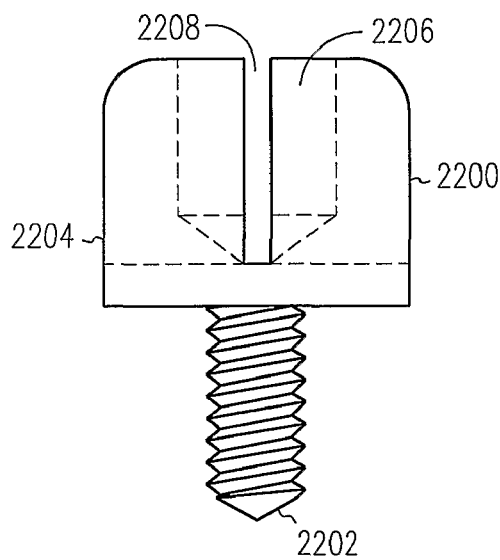
FIG. 22 is a cross-sectional schematic diagram illustrating a bone screw base with a head that includes an orifice for receiving a shaft portion of an imageable marker or locatable divot, and which further includes screwdriver slots or other features that permit the bone screw base to be driven into the skull.

FIG. 22 is a cross-sectional schematic diagram illustrating a bone screw base 2200 that includes an externally threaded distal shaft 2202 and a proximal head 2204. The proximal head 2204 includes an orifice 2206 for receiving a shaft portion of an imageable marker or locatable divot that is press or snap fitted therein. The head 2204 also includes screwdriver slots 2208 or other features that permit the bone screw base 2200 to be driven into the skull, as illustrated in the top view of FIG. 23.

Figure 25:
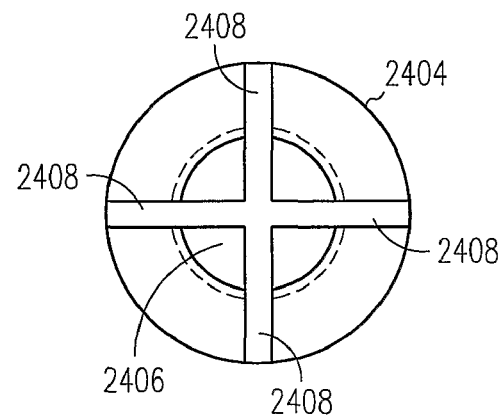
FIG. 25 illustrates a top view of the fiducial marker base of FIG. 24.
Figure 24:
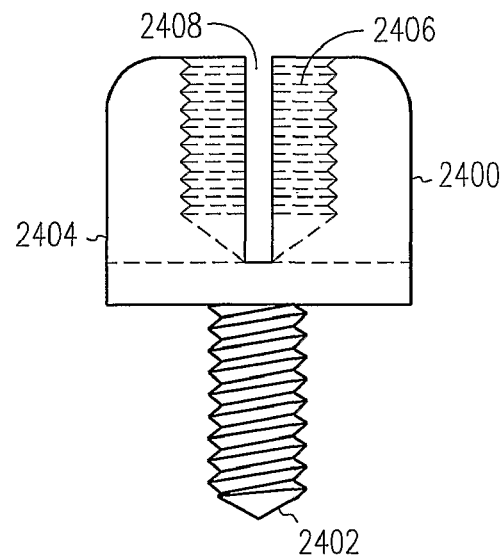
FIG. 24 is a cross-sectional schematic diagram illustrating a bone screw base with a head that includes an internally threaded orifice for receiving an externally threaded shaft portion of an imageable marker or locatable divot, and which further includes screwdriver slots or other features that permit the bone screw base to be driven into the skull.

FIG. 24 is a cross-sectional schematic diagram illustrating a bone screw base 2400 that includes an externally threaded distal shaft 2402 and a proximal head 2404. The proximal head 2404 includes an internally threaded orifice 2406 for receiving an externally threaded shaft portion of an imageable marker or locatable divot that is threaded therein. The head 2404 also includes screwdriver slots 2408 or other features that permit the bone screw base 2400 to be driven into the skull, as illustrated in the top view of FIG. 25.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. An assembly for an image-guided surgical procedure, the assembly comprising:
   a fiducial marker;
   a bone screw base, the base including a distal threaded bone screw shaft and a proximal head, the proximal head having a receptacle formed in a proximal end thereof and configured to receive at least a portion of the fiducial marker therein; and
   a protective sleeve removably fitted around an outer perimeter of the proximal head of the bone screw base, the protective sleeve including a compliant valve in a proximal end thereof that automatically opens upon insertion of an object into the valve and that automatically closes upon removal of the object from within the valve, the protective sleeve having an axial length greater than an axial length of the proximal head such that the proximal end of the protective sleeve extends beyond and is spaced apart from the proximal end of the proximal head when fitted thereto, the protective sleeve covering the receptacle when the compliant valve is in a closed position.

2. The assembly of claim 1, wherein the fiducial marker is sized and shaped to be secured to the first receptacle formed in the proximal head of the bone screw base.

3. The assembly of claim 1, further comprising a locatable divot that is sized and shaped to be secured to the proximal head of the bone screw base.

4. The assembly of claim 1, wherein the sleeve comprises a sidewall extending from the proximal end to a distal end thereof, the sidewall being removably fitted around the outer perimeter of the proximal head and forming an internal passage between the valve and the proximal head of the bone screw base.

5. The assembly of claim 1, wherein the compliant valve includes a tricuspid valve.

6. The assembly of claim 1, wherein the proximal head of the bone screw base includes a radially inwardly extending recess, and wherein the sidewall of the protective sleeve includes a radially inwardly extending lip sized and shaped to engage the recess when the sleeve is removably fitted around the proximal head.

7. The assembly of claim 1, wherein the proximal head defines a slot formed through at least a portion of the receptacle and adapted to receive a driver therein.

8. A kit comprising:
   a bone screw base, the base comprising a distal threaded bone screw shaft and a proximal head including a receptacle formed in a proximal end thereof; and
   a protective sleeve having a sidewall extending from a proximal end to a distal end, the proximal end including a compliant tricuspid valve that automatically opens upon insertion of an object into the valve and that automatically closes upon removal of the object from within the valve, the sidewall of the protective sleeve removably fitted around an outer perimeter of the proximal head such that the proximal end of the protective sleeve is spaced apart from the proximal end of the proximal head and covers the proximal head and the receptacle when the valve is in a closed position.

9. The kit of claim 8, further comprising an imageable marker that is sized and shaped to be secured to the receptacle formed in the proximal head of the bone screw base.

10. The kit of claim 8, further comprising a locatable divot that is sized and shaped to be secured to the receptacle formed in the proximal head of the bone screw base.

11. The kit of claim 8, further comprising the sidewall of the protective sleeve having an axial length greater than an axial length of the proximal head such that the protective sleeve extends beyond the proximal end of the proximal head when fitted thereto and forms an internal passage between the proximal end of the sleeve, the sidewall and the proximal head.

12. The kit of claim 8, wherein the proximal head defines a slot formed through at least a portion of the receptacle and adapted to receive a driver therein.

13. The kit of claim 8, wherein the sidewall of the protective sleeve covers an entire axial length of the proximal head.

14. The kit of claim 8, wherein the sidewall defines a shoulder, the shoulder engaging the proximal end of the proximal head.

15. A method comprising:
  removably coupling a valved sleeve around an outer perimeter of a proximal head of a bone screw base, the valved sleeve having a compliant valve formed in a proximal end thereof, the bone screw base including a distally extending threaded shaft;
  passing a shaft of a tool through the compliant valve and into engagement with an internal receptacle formed in a proximal end of the proximal head;
  maintaining engagement of the bone screw base with the shaft of the tool via engagement of the compliant valve with the shaft of the tool prior to affixing the bone screw base to a skull;
  affixing the bone screw base to the skull via the distally extending shaft;
  removing the shaft of the tool from the bone screw base and the valved sleeve, the compliant valve automatically closing after removal of the tool to cover the proximal head and the internal receptacle;
  attaching an imageable marker to the proximal head of the bone screw base, including inserting a portion of the imageable marker through the compliant valve; and
  replacing the imageable marker with a locatable divot, the replacing including removing the imageable marker from the proximal head and inserting the locatable divot through the compliant valve and into the proximal head.

16. The method of claim 15, in which the inserting the portion of the imageable marker through the valve automatically opens the valve by compliant expansion of the valve, and in which the removing the imageable marker includes automatically closing the valve by compliant relaxation of the valve.

17. The method of claim 15, wherein removably coupling a valved sleeve around an outer perimeter of a proximal head of a bone screw base includes positioning a radially inwardly extending lip of the valved sleeve in a corresponding recess of the bone screw base.

18. The method of claim 15, wherein removably coupling a valved sleeve around an outer perimeter of a proximal head of a bone screw base includes removably coupling the valved sleeve around the outer perimeter of the bone screw base such that the proximal end of the valved sleeve is spaced apart from the proximal head and the valved sleeve forms an internal passage between the complaint valve and the proximal head.

* * * * *